United States Patent [19]
Kane

[11] 3,932,869
[45] Jan. 13, 1976

[54] TACTILE NUMERIC DISPLAY DEVICE

[76] Inventor: Gabriel Kane, Manhattan College, Manhattan College Parkway, Bronx, N.Y. 10471

[22] Filed: Oct. 11, 1974

[21] Appl. No.: 513,995

Related U.S. Application Data

[63] Continuation-in-part of Ser. No. 420,956, Dec. 3, 1973, abandoned.

[52] U.S. Cl............ 340/407; 35/35 A; 128/419 PG
[51] Int. Cl.² ......................................... G08B 1/00
[58] Field of Search ..... 340/407; 35/35 A; 128/418, 128/419 PG

[56] References Cited
UNITED STATES PATENTS

| | | | |
|---|---|---|---|
| 2,703,344 | 3/1955 | Anderson | 35/35 A X |
| 3,108,268 | 10/1963 | Uttal | 340/407 |
| 3,395,247 | 7/1968 | Fieldgate | 340/407 X |
| 3,612,061 | 10/1971 | Collins | 340/407 X |
| 3,628,193 | 12/1971 | Collins | 340/407 |

*Primary Examiner*—John W. Caldwell
*Assistant Examiner*—William M. Wannisky

[57] ABSTRACT

A tactile numeric display apparatus comprises a plurality of concentric electrical conductor pairs extending from a panel of insulating material. The conductor pairs are arrayed in Braille groups to represent decimal positional notation. The conductor pairs selectively receive a periodic bipolar constant current pulse so that by feeling a current in the fingers when on particular conductor pairs a user can determine which numbers are displayed.

3 Claims, 11 Drawing Figures

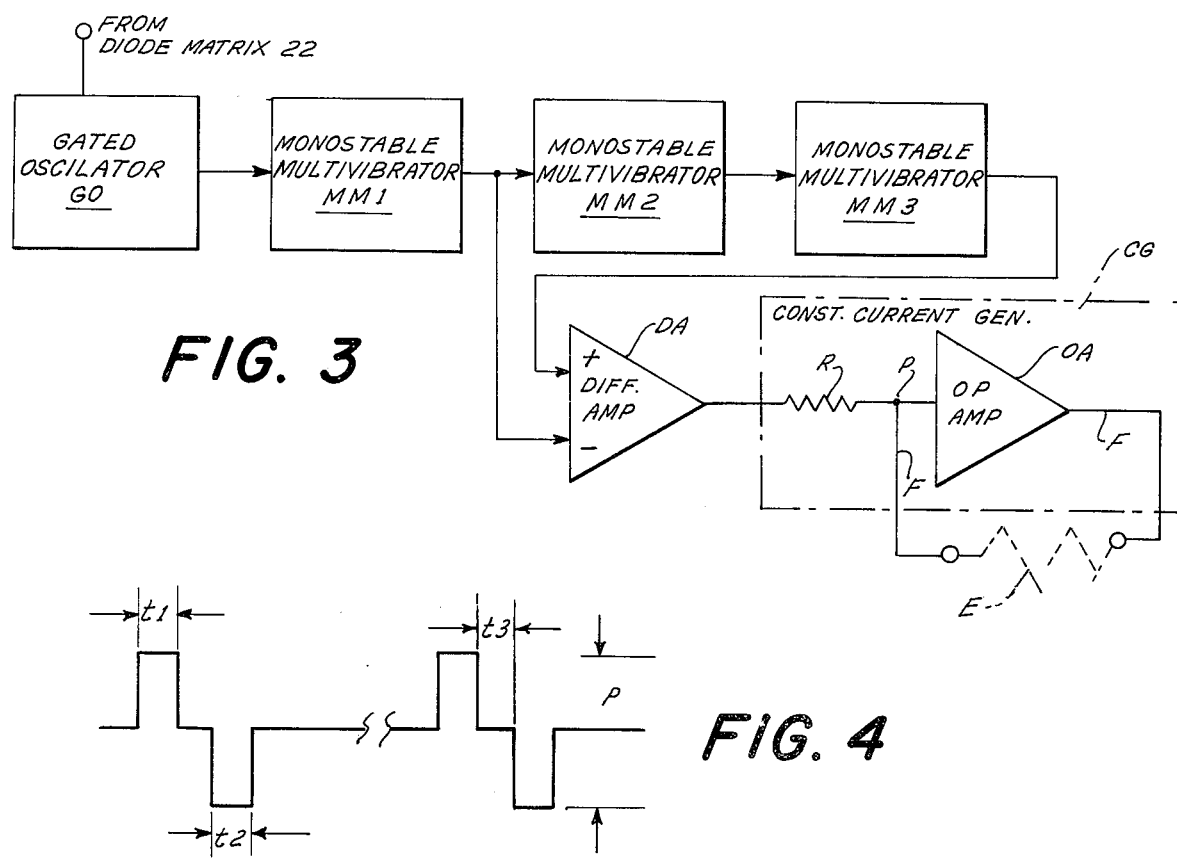
FIG. 3
FIG. 4
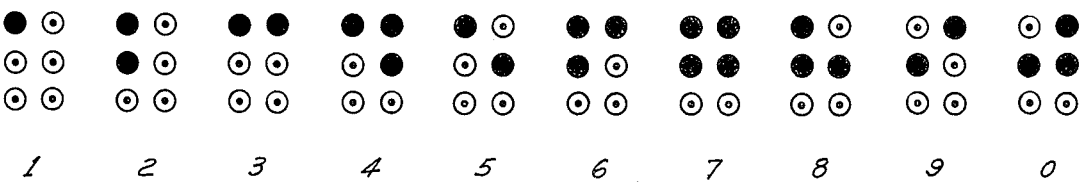
FIG. 6
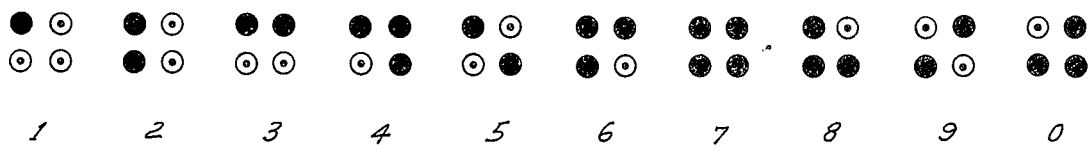
FIG. 7

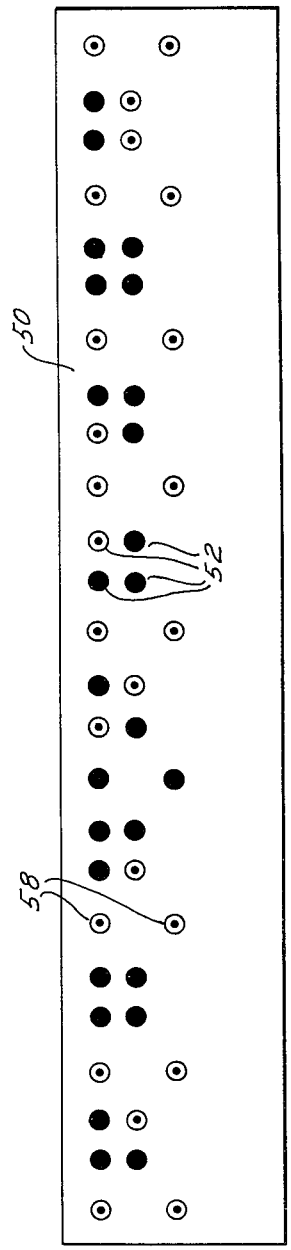
FIG. 8A
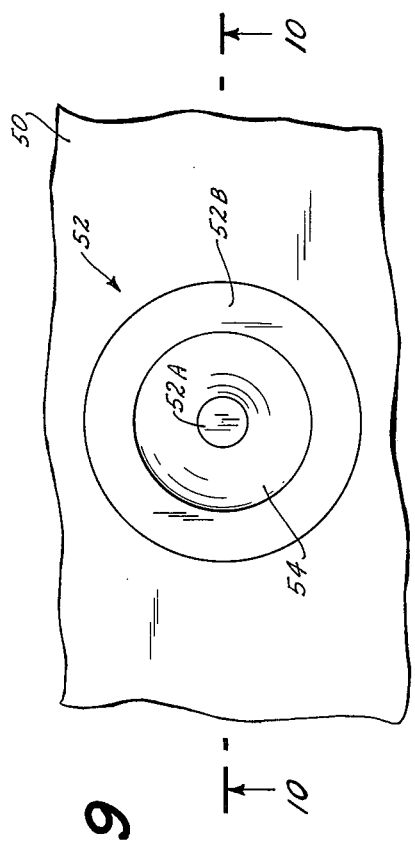
FIG. 8B
674.98073
FIG. 9
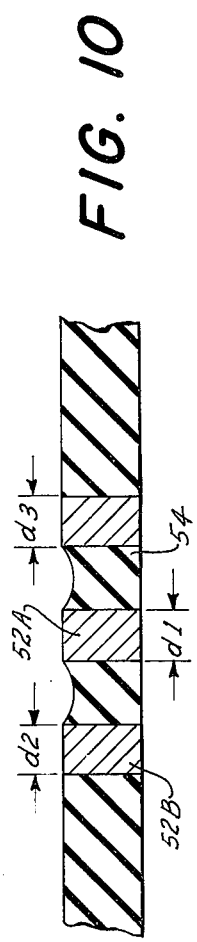
FIG. 10

TACTILE NUMERIC DISPLAY DEVICE

This application is a continuation-in-part of my co-pending application Ser. No. 420,956, filed Dec. 3, 1973 and now abandoned.

THE INVENTION

This invention pertains to display devices and more particularly to devices for conveying information by the electrical stimulation of the finger tips of a user.

An object of the invention is to display in a cutaneous form information which is usually presented visually.

There are many blind people today who could successfully have a more useful role in society if they had access to usable numeric output devices such as calculators, computers and digital meters. While it is true that output devices using solenoid operated pins are available, such output devices are often so complex and expensive as to prohibit their use with existing equipment. For example, there are available today hand and desk calculators that retail for considerably less than One Hundred Dollars. Therefore, it is only reasonable to demand that the display part of such a calculator cost only a minor fraction of the entire cost of the system.

It is accordingly a general object of the invention to provide a display device which can be used by a sightless person.

It is another object of the invention to provide such a display device which, while being less expensive than previously available devices, is also more rugged and reliable.

These and other objects are satisfied by the invention which contemplates a tactile numeric display apparatus comprising a panel of insulating material carrying a plurality of concentric electrical conductor pairs. Each of the electrical conductors of each pair has at least one end extending through the top surface of the panel so that it can be touched by a user. The electrical conductor pairs are arrayed in decimal positional notation with each character in Braille representation. The electrical conductors are selectively energized to transmit bipolar pulses from a constant current source.

Other objects, the features and advantages of the invention will be apparent from the following detailed description when read with the accompanying drawing which shows several embodiments of the invention.

In the Drawing:

FIG. 3 is a logic diagram of a typical pulse generator used by the translator of FIG. 2;

FIG. 4 is a waveform diagram of the pulses generated by the pulse generator of FIG. 3;

FIG. 6 shows the Braille representations for the decimal digits;

FIG. 7 shows a modification of the representation of FIG. 6;

FIG. 8A shows an embodiment of the display device utilizing the modified Braille representation of the digits with FIG. 8B showing the number present on the display device of FIG. 8A.

FIG. 9 shows an enlarged plan view of a part of the display device of FIG. 8A; and FIG. 10 shows a section through the line 10—10 of FIG. 9.

Figure 1:
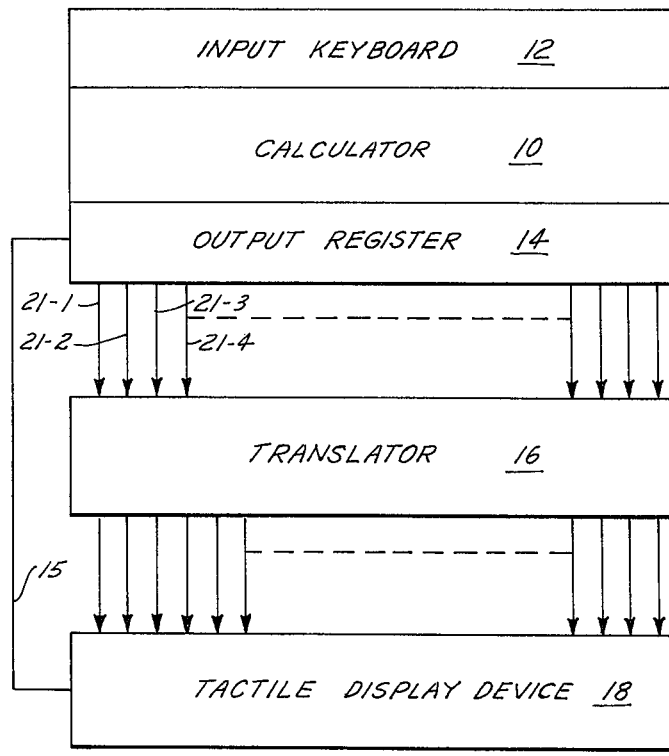
FIG. 1 is a block diagram of a calculator system utilizing the invention.

In FIG. 1 there is shown a calculator system comprising a calculator 10 having an input keyboard 12 and an output register 14 which is connected via a translator 16 to a tactile display device 18.

The calculator 10 can be a conventional electronic calculator having the usual complement of registers and an arithmetic unit. Entries are made into the calculator via keyboard 12 which in addition to the numberic keys includes the arithmetic function keys. The results of calculations are stored in an output register 14 which can be a flip-flop register having four flip-flops per decimal position wherein the results are stored in binary-coded decimal form. Such a calculator and its associated output register is well known in the art and need not further be described.

If one assumes an eight digit calculator then the output register will have eight stages each of four flip-flops. Therefore, each stage will have four output terminals and the binary coded combination of signals on those terminals represents the digit stored in the stage. The four terminals of each stage are connected via four lines to four input terminals of the translator 16. FIG. 1 shows only the connections from the most and least significant stages of the output register 14. However, it should be realized that there are similar connections from each of the intermediate stages.

In addition, line 15 represents a cable connecting the floating decimal point register of the calculator 10 to the tactile display device 18.

Figure 2:
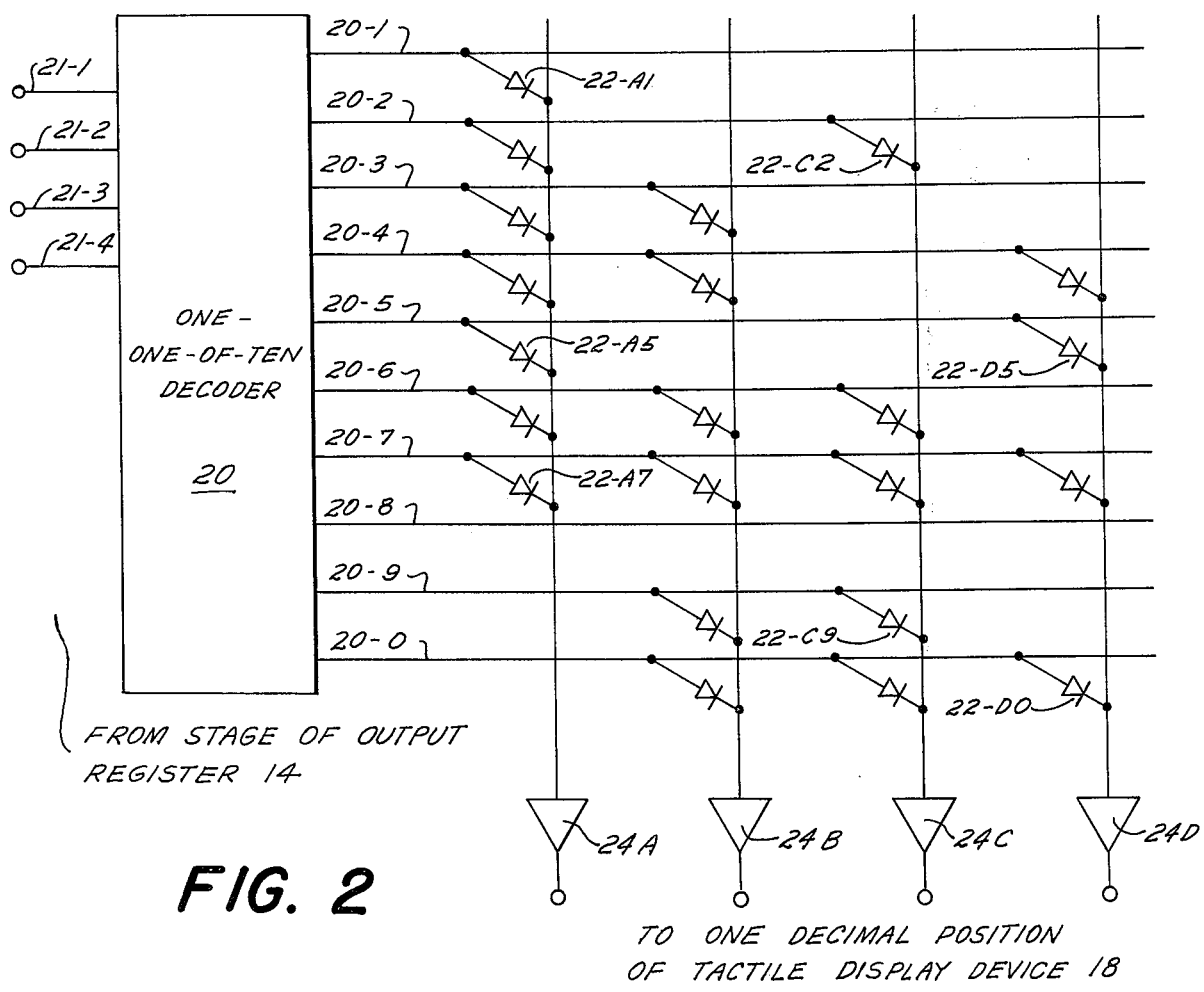
FIG. 2 is a logic diagram of a translator used in the system of FIG. 1.

The translator 16 is basically a decoder which changes the coded combinations of signals received at its input terminals to a different coded combination of signals at its output terminal. The translator 16 has the same number of stages as the output register 14 with each stage of the translator 16 being associated with a given stage of the output register 14. The construction of a translator stage is determined by the type of display device used. For example, for a tactile display device wherein each digit is represented by four binary bits or Braille bosses one should use a translator stage as shown in FIG. 2. The stage comprises conventional one-out-of-ten decoder 20, the diode matrix 22 and the pulse generators 24. When a binary coded digit is received at the inputs 21-1 to 21-4 of decoder 20 it generates a signal on one of the lines 20-1 to 20-0. This signal is transferred by the diodes of the matrix to a combination of the pulse generators 24A to 24D. (As will hereinafter become apparent these combinations of four signals can be used to represent the Braille numeric digits.) For example, if the signals on the inputs 21-1 to 21-4 of decoder 20 are the binary-coded representation of the decimal digit 95, then decoder 20 will emit a signal of line 20-5. This signal will be fed via diode 22-A5 to pulse generator 24A and via diode 22-D5 to pulse generator 24D. The signals from pulse generators 24A and 24D are fed to those electrical conductors in tactile display device 18 which would represent the digit five in a modified Braille notation.

Figure 5:
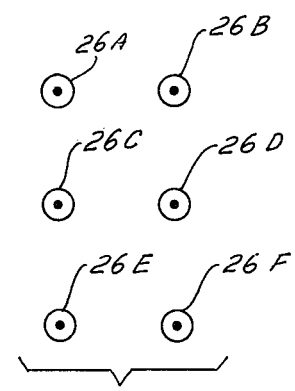
FIG. 5 is a diagram of the locations of the indicia which define a Braille character.

FIG. 5 shows a typical format for a Braille character. The character is represented by raised bosses in a combination of the six positions indicated by open circles 26A to 26F. Now it so happens that the decimal digits 0 through 9 do not have any bosses in positions 26E and 26F. Therefore, for numerics one requires four signals. These signals are generated by the pulse generators 24A to 24D which are in one-to-one correspondence with bosses 26A to 26D, respectively.

A typical pulse generator 24A is shown in FIG. 3 while the current waveform generated by the pulse generator is shown in FIG. 4. The amplifier comprises a gated free running oscillator FRO which can be a conventional relaxation oscillator such as an assymetrical astable multivibrator that is biased off when a low signal is present at its control input C and oscillates freely when the signal at the control input goes high to produce positive going pulses which periodically occur at a given rate. The output of the oscillator FRO is connected to the input of monostable multivibrator MM1. The multivibrator of conventional design is triggered to emit a negative going pulse of given duration each time it receives the negative going trailing edge of a pulse from oscillator FRO. The output of monostable multivibrator MM1 is connected to the input of monostable multivibrator MM2. This multivibrator is the same as monostable multivibrator MM1 and is triggered to emit a positive going pulse of the same given duration each time it receives the negative going trailing edge of a pulse from monostable multivibrator MM1. The output of monostable multivibrator MM2 is connected to the input of monostable multivibrator MM3 which is the same as monostable multivibrator MM1 and is triggered to emit a positive going pulse of the same duration each time it receives the negative going trailing edge of a pulse from monostable multivibrator MM2.

The outputs of the monostable multivibrators MM1 and MM3 are fed to the respective inputs of convention difference amplifier DA whose output transmits the composite waveform shown in FIG. 4. The voltage signal is fed to the constant current generator CCG comprising conventional operational amplifier OA, input resistor R and feedback path F with the point P at virtual ground. Within the feedback path is connected an electrical conductor pair hereinafter more fully described but for the present is represented by dotted line resistor E. Thus passing through the feedback path is a current having the waveform of FIG. 4.

It has been found that for best results the pulse repetition rate should be of 20 to 250 pulses per second while the width $t1$ and $t2$ of both the positive and negative lobes should be in the range of from 0.1 to 1 millisecond. The negative lobe should be delayed after the positive lobe by a length of time $t3$ equal to the pulse width of either lobe. Finally the pulses should have a peak to peak amplitude $p$ of from 0.5 to 10 milliamperes.

While a decimal matrix panel can be used as a display device, it is much simpler and more easily readable to use a Braille type display. Before describing such a display there will first be a discussion of the decimal digits as represented in Braille. In FIG. 6 there is shown such a representation of the digits.

It will be recalled that there is no need to represent the pair of bosses in the lowest row of each character since they never occur for the decimal digits. Therefore, for a pure numeric display the decimal digits can be represented by the modified Braille configurations shown in FIG. 7. When using these modified Braille configurations one can construct the display device shown in FIGS. 8 to 10.

The display device comprises the panel 50 of insulating material carrying eight sets of four conductor pairs 52 wherein each set is arrayed to simulate the four possible bosses of a modified Braille digit. It should be noted that between each set of conductor pair 52 is a dual of conductor pairs 58 which represent a decimal point. As shown in FIGS. 9 and 10 each conductor pair 52 comprises a central conductor 52A and an annular conductor 52B concentric therewith. Each conductor has a top extending above panel 50 and a bottom which can be connected via wires to the outputs of translator 16 and more particularly to the outputs of pulse generators 24A to 24D (See FIG. 2).

Furthermore, the annulus 54 of insulating material which separates central conductor 52A from annular conductor 52B has a depression so that any perspiration left after touching by the user tends to accumulate in the trough so formed thus preventing any undesired conductive bridging of the gap.

It has been found that the diameter $D1$ of the central conductor is preferably from 3/64 to ⅛ inch in diameter; the width $d2$ of the annular conductor should be between 1/32 and 1/16 of an inch; and the gap $D3$ between the conductors should be between 3/64 and ⅛ of an inch. Finally, the ratio of the exposed area of conductor 52A to that of conductor 52B should be less than or equal to 1:4.

In operation when the calculator system displays a character, translator 16 transmits suitably pulsed current via A cable to the appropriate conductor pairs 52 and 58. A user now may sweep his forefinger from left to right along the sets of conductor pairs 52 and 58. The tingling sensations in the energized conductor pairs 52 and will be interpreted as decimal digits. Note in FIG. 8 the black electrode pairs are the ones being energized to display the number 674.98073.

While a preferred embodiment has been shown and described in detail, there will now be obvious to those skilled in the art many modifications and variations satisfying many or all of the objects of the invention but which do not depart from the spirit thereof as defined by the appended claims.

What is claimed is:

1. A tactile numeric display apparatus comprising: a panel of insulating material; a plurality of sets of four electrical conductor pairs, the four electrical conductor pairs of each set being disposed in said panel of insulating material at the corners of quadrilaterals to simulate abbreviated Braille representation of Arabic numerals, each of the electrical conductor pairs including a central conductor having a diameter of from 3/64 to ⅛ inch, and a surrounding concentric annular conductor having a width of from 1/32 to 1/16 inch, with the separation of the conductors of the pair being from 3/64 to ⅛ inch, and the operative area of the central conductor being no greater than one-fourth of the operative area of the said annular conductor, each of the conductors of each electrical conductor pair having at least one end extending beyond one of the surfaces of said panel so that it can be touched by a user; a pulse generator means including a plurality of constant current sources, each of said constant sources having an input and an output connected to one of said pairs of electrical conductors, a plurality of bipolar waveform generators, each of said bipolar waveform generators having an input and an output connected to the input of one of said constant current sources, respectively, each of said bipolar waveform generators when activated generating from 20 to 250 pulse pairs per second, wherein each pair comprises a positive pulse of from 0.1 to 1 millisecond duration and a negative pulse of from 0.1 to 1 millisecond duration with a time interval between the positive and negative pulses of each pair being equal to the duration of one of said pulses and the peak to peak amplitude from the positive pulse to the negative pulse being such that the peak to peak current flowing from said constant current sources is between 0.5 and 10 milliampere; and means for selectively energizing said bipolar waveform generators in accordance with the Arabic numerals to be displayed.

2. The apparatus of claim 1 wherein said sets of four electrical conductor pairs are disposed along a straight line in said panel and further comprising at least a single further electrical conductor pair disposed between each of said sets.

3. The apparatus of claim 2 where each of said bipolar waveform generators comprises a gated oscillator operating at a frequency of from 20 to 250 Hz and having an input connected to said selectively energizing means and an output, three monostable multivibrators connected in cascade to the output of said gated oscillator, each of said monostable multivibrators when triggered emitting a pulse having a duration of from 0.1 to 1 milleseconds, a difference amplifier having a positive and negative input and an output, one of said inputs being connected to the output of the monostable multivibrator directly connected to said gated oscillator, the other of said inputs being connected to the output of the monostable multivibrator most remote from said gated oscillator, and means for connecting the output of said difference amplifier to the input of a constant current source.

\* \* \* \* \*